US006827442B2

(12) United States Patent
Ross et al.

(10) Patent No.: US 6,827,442 B2
(45) Date of Patent: Dec. 7, 2004

(54) OPHTHALMIC WAVEFRONT MEASURING DEVICES

(76) Inventors: Denwood F. Ross, 8420 Center Rd. South, Austinburg, OH (US) 44010; Josef Bille, Hermann-Loens-Weg 44/1, Heidelberg (DE), D-69181; Michael Schottner, Richard-Wagner Strasse 20, Liemen (DE), D-69181; Frank Mueller, St.-German-Str. 23, Speyer (DE), 67346

( * ) Notice: Subject to any disclaimer, the term of this patent is extended or adjusted under 35 U.S.C. 154(b) by 0 days.

(21) Appl. No.: 09/950,916

(22) Filed: Sep. 12, 2001

(65) Prior Publication Data

US 2003/0048413 A1 Mar. 13, 2003

(51) Int. Cl.[7] .............................. A61B 3/00; A61B 3/10; G01J 1/20
(52) U.S. Cl. ..................... 351/205; 250/201.9; 351/246
(58) Field of Search ................................. 351/205, 206, 351/211, 212, 221, 246; 250/201.9; 359/224

(56) References Cited

U.S. PATENT DOCUMENTS

| 4,824,243 A | * | 4/1989 | Wheeler et al. ............. 356/121 |
| 4,838,679 A | | 6/1989 | Bille |
| 4,943,709 A | * | 7/1990 | Grinberg et al. ............ 356/121 |
| 4,950,878 A | * | 8/1990 | Ulich et al. ............... 250/201.9 |
| 5,062,702 A | | 11/1991 | Bille |
| 5,177,511 A | | 1/1993 | Feuerstein et al. |
| 5,229,889 A | * | 7/1993 | Kittell ......................... 359/849 |
| 5,777,719 A | * | 7/1998 | Williams et al. ............ 351/212 |
| 5,785,704 A | | 7/1998 | Bille et al. |
| 5,949,521 A | | 9/1999 | Williams et al. |
| 6,042,233 A | | 3/2000 | Mihashi et al. |
| 6,095,651 A | | 8/2000 | Williams et al. |
| 6,155,684 A | | 12/2000 | Bille et al. |
| 6,486,943 B1 | * | 11/2002 | Burns et al. ................ 356/124 |
| 2002/0180931 A1 | * | 12/2002 | Dick et al. .................. 351/211 |

FOREIGN PATENT DOCUMENTS

| DE | 4222395 | 1/1994 |
| WO | WO 99/27334 | 6/1999 |
| WO | WO 01/06914 A | 2/2001 |
| WO | WO 01/28408 A | 4/2001 |
| WO | WO 01/58339 A | 8/2001 |

OTHER PUBLICATIONS

G. Walsh, W.N. Charman and H.C. Howland, Objective Technique for the Determination of Monochromatic Aberrations of the Human Eye:, Sep. 1984, vol. 1, No. 9, pp. 987–992.

Andreas W. Dreher, Josef F. Bille, and Robert N. Weinreb, "Actove Optical Depth Resolution Improvement of the Laser Tomographic Scanner", Feb. 15, 1989, vol. 28, No. 4, pp. 804–808.

(List continued on next page.)

Primary Examiner—Brian L. Casler
Assistant Examiner—John R. Sanders

(57) ABSTRACT

Apparatuses and methods for improving aberration determination capabilities, providing corrective prescription verification, and allowing binocular vision correction in ophthalmic wavefront measuring devices. (1) Improved aberration determination capabilities are achieved through input beam modification which includes sensing an image in a wavefront emanating from an eye in response to an input beam with a sensor and then modifying the input beam with an adaptive optical device based on the sensed information. (2) Corrective prescription verification includes modifying an image with an adaptive optical element to produce a corrected image at the patients eye. (3) Binocular vision correction for a pair of eyes includes measuring the aberrations of one eye with a first ophthalmic wavefront measuring device and measuring the aberration produced by the other eye with a second ophthalmic wavefront measuring device substantially simultaneously.

2 Claims, 9 Drawing Sheets

OTHER PUBLICATIONS

W.N. Charman, "Wavefront Aberration of the Eye: A Review", Optometry and Vision Science, Symposium Paper, Feb. 26, 1991, vol. 68, No. 8, pp. 574–583.

Junzhong Liang, Bernhard Grimm, Stefan Goelz, and Josef Bille, "Objective Measurement of Wave Aberrations of the Human Eye With the Use of a Hartmann–Shack Wavefront Sensor", Jul. 1994, vol. 11, No. 7, pp. 1–9.

D.R. Williams and J. Liang, "Adaptive Optics for High Resolution Retinal Imaging", Feb. 15, 1996, vol. 37, No. 3, 1 page.

Josef Bille, Andreas W. Dreher and Gerhard Zinser, "Scanner Laser Tomography of the Living Human Eye", Chapter 28, pp. 528–547, date unknown.

Dirk–Uwe Bartsch, PhD, Gerhard Zinser, PhD, and William R. Freeman, M.D., "Resolution Improvement in Confocal Scanning Laser Tomography of the Human Fundus", pp. 134–137, date unknown.

Bille, J.F., Preoperative Simulation fo Outcomes Using Adaptive Optics, Journal of Refractive Surgery, United States, vol. 16, No. 5, pp. S608–S610, Sep. 2000.

Marcos, S. et al., On the Symmetry Between Eyes fo Wavefront Aberration and Cone Directionality, Vision Research, England, vol. 40, No. 18, pp. 2437–47 (2000).

PCT Int'l. Search Report, dated May 27, 2003, for PCT Appln. No. PCT/US02/2743.

* cited by examiner

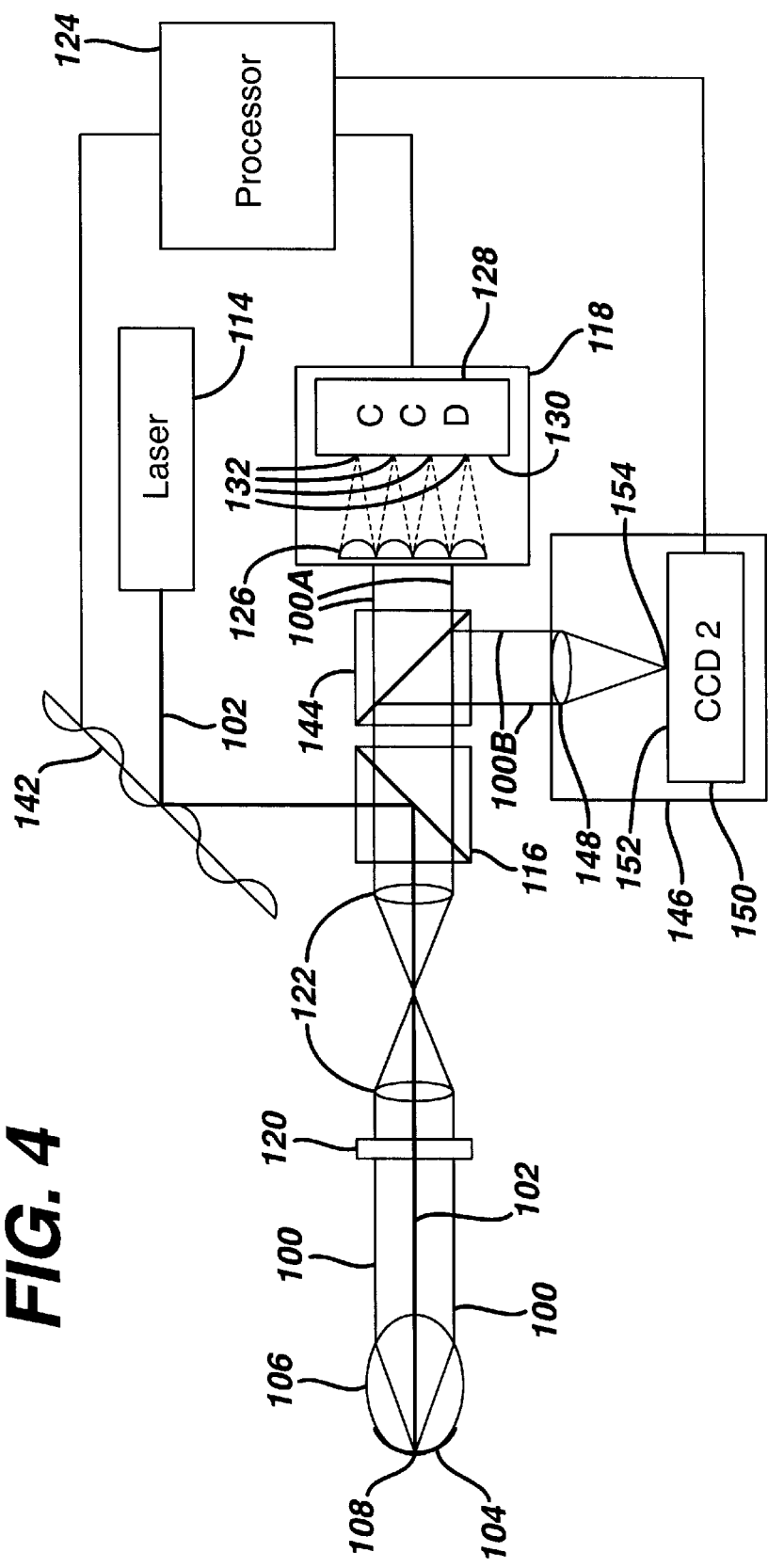

OPHTHALMIC WAVEFRONT MEASURING DEVICES

FIELD OF THE INVENTION

The present invention relates generally to optical instruments for measuring eye aberrations in a patient and, more particularly, to apparatuses and methods for modifying the input beam entering the patient's eye, patient corrective prescription verification, and binocular vision correction in ophthalmic wavefront measuring systems.

BACKGROUND OF THE INVENTION

The eye is an optical system having several lens elements for focusing light rays representing images onto the retina within the eye. The sharpness of the images produced on the retina is a factor in determining the visual acuity of the eye. Imperfections within the lens and other components and material within the eye, however, may cause the light rays to deviate from the desired path. These deviations, referred to as aberrations, result in blurred images and decreased visual acuity. Hence, methods and apparatuses for measuring aberrations are used to aid in the correction of such problems.

One method of detecting aberrations introduced by the eye involves the determination of aberrations introduced into light rays when exiting from the eye. An input beam of light focused into the eye to a point on the retina is reflected or scattered back out of the eye as a wavefront, with the wavefront containing aberrations introduced by the eye. By determining the propagation direction of discrete portions (i.e., samples) of this wavefront, the aberrations introduced by the eye can be determined. The determined aberrations can then be used to produce corrective lenses and/or perform corrective procedures that restore visual acuity.

A general illustration of the generation of a wavefront is shown in FIG. 1. A wavefront 100 is generated by reflecting an input beam 102 off of the retina 104 of an eye 106. The input beam 102 focuses to a small spot 108 on the retina 104. The retina 104, acting as a diffuse reflector, reflects the input beam 102, resulting in the wavefront 100. Ideally, the wavefront 100 would be free of aberrations, as illustrated by the planar wavefront 110. However, aberrations introduced by the eye 106 as the wavefront 100 passes out of the eye 106 result in an imperfect wavefront, as illustrated by the aberrated wavefront 112. The wavefront 100 represents aberrations due to defocus, astigmatism, coma, spherical aberrations, and other irregularities. Measuring and correcting the aberrations allow the eye 106 to approach its full potential, i.e., the limits of visual resolution.

FIG. 2 is an illustration of a prior art ophthalmic wavefront measuring device for measuring aberrations within the wavefront 100 as illustrated in FIG. 1. A radiation source 114 (e.g., a laser) generates the input beam 102 which is routed to the eye 106 by a beam splitter 116. Typically, the input beam 102 generated by the radiation source 114 is substantially circular. The input beam 102 forms a spot 108 on the retina 104 of the eye 106. In an eye 106 free of imperfections, the spot 108 formed on the retina 104 is circular. Due to imperfections within the eye 106, the input beam 102 becomes aberrated, thereby resulting in the spot 108 formed on the retina 104 having a non-circular shape as illustrated in FIG. 2A. As will be discussed below, a retinal spot 108 with a non-circular shape affects adversely the determination of aberrations due to imperfections within the eye 106. The retina 104 then reflects the light from the spot 108 to create a wavefront 100 which is aberrated as it passes through the lens and other components and materials within the eye 106.

On the return path, the wavefront 100 passes through the beam splitter 116 toward a sensor 118. A quarter-wave plate 120 is positioned between the eye 106 and the beam splitter 116. The use of a quarter-wave plate 120 is a known technique for manipulating the polarization of the input beam 102 going into the eye 106 and the wavefront 100 emanating from the eye 106 so that the wavefront 100 is polarized in a direction perpendicular to the input beam 102, thereby enabling the wavefront 100 to pass through the beam splitter 116 toward the sensor 118. Additional lenses 122 are positioned between the eye 106 and the sensor 118 to image the plane of the pupil of the eye 106 onto the sensor 118 with a desired magnification. Information detected by the sensor 118 is then processed by a processor 124 to determine the aberrations of the wavefront 100 and determine a corrective prescription for the eye 106.

A typical sensor 118 includes a Hartman-Shack lenslet array 126 and an imaging device 128 containing an imaging plane 130 such as a charge coupled device (CCD) array. The lenslet array 126 samples the wavefront 100 and produces an array of spots 132 on the imaging plane 130, as illustrated in FIG. 2B, when the wavefront 100 passes through it. Each spot within the array of spots 132 is an image of the retinal spot 108. The relative positions of each spot within the array of spots 132 can be used to determine the aberrations of the wavefront 100.

Typically, the aberrations of the wavefront 100 are determined by determining an aberration for each sample of the wavefront 100 which are then combined. The determined aberrations are then used to calculate a corrective prescription for the eye 106.

The aberration of each sample of the wavefront 100 is determined by determining the centroid of a spot within the array of spots 132 and comparing the displacement between the centroid of the spot with a corresponding reference location, such as the location represented by reference spot 134. Since each spot within the array of spots 132 is an image of the retinal spot 108, if the retinal spot 108 is non-circular, as illustrated in FIG. 2A, each spot within the array of spots 132 will be non-circular, as illustrated in FIG. 2B.

Determining the centroid of a non-circular spot, however, is difficult, requiring significant processing time and power. Accordingly, since determining the centroid of the spots within the array of spots 132 is a prerequisite to determining the aberrations in the wavefront 100, and determining the centroid of a non-circular spot is difficult, non-circular spots on the imaging plane 130 affect adversely the speed and accuracy of computing aberrations. Therefore, apparatuses and methods for producing circular spots on the imaging plane 130 would be useful.

Another area for improvement is related to the ability of wavefront measuring devices to determine aberrations introduced by the eye 106 with a high degree of accuracy. This accuracy allows the determination of a corrective prescription for a patient that is precisely tailored to the patient's visual needs. The precisely tailored corrective prescriptions, however, cannot be presented to the patient through a series of lenses as is traditionally done in determining corrective prescriptions at an eye doctor for example. This is due to the fact that each precisely tailored corrective prescription is so unique that it would be impossible to recreate the corrective prescription using a series of lenses without specially producing a lens having the corrective prescription. Accordingly, the patient is unable to determine if the corrective prescription determined by the wavefront measuring device satisfies the patient's visual needs until prescription eye wear is produced (e.g., corrective lenses are ground or contact lenses are formed). Therefore, apparatuses and methods for allowing a patient to verify a corrective prescription prior to the production of corrective eye wear would be useful.

Yet another area for improvement is related to the dependancy of aberrations on binocular vision (i.e., viewing an object with both eyes at the same time). Prior art wavefront measuring devices such as the one depicted in FIG. 2 measure only one eye at a time. Accordingly, the affects of binocular vision on aberrations are not taken into consideration when developing corrective prescriptions and, therefore, the limits of visual resolution are not achieved in traditional wavefront aberration measuring devices. Therefore, wavefront measuring apparatuses and methods having binocular measurement capabilities would be useful.

SUMMARY OF THE INVENTION

The present invention discloses apparatuses and methods for improved aberration determination, corrective prescription verification, and binocular vision correction in wavefront measuring devices.

One aspect of the present invention is an input beam modifying apparatus and method for modifying an input beam into an eye for use with a wavefront measuring device to improve the measurement of aberrations. By modifying the input beam, the shape of an image formed on an imaging plane in a wavefront measuring device can be controlled to form a desired image, thereby facilitating calculations involved in determining aberrations. The input beam modifying apparatus comprises a sensor for sensing the image in the wavefront emanating from the eye in response to the input beam, an adaptive optical device for modifying the input beam, and a processor for receiving information from the sensor and adjusting the adaptive optical device to modify the input beam to produce a desired image at the sensor. The method for modifying the input beam includes sensing an image within a wavefront emanating from the eye in response to the input beam, and modifying the input beam to produce a desired image being sensed.

Another aspect of the present invention is a corrective prescription verification apparatus and method for use with a wavefront measuring device capable of generating information related to aberrations introduced by an eye. The corrective prescription verification apparatus and method enable a wavefront measuring device to present an image to a patient as it would appear if the patient were wearing corrective eye wear having a corrective prescription as determined by the wavefront measuring device. The corrective prescription verification apparatus includes a projector capable of emitting an image, an adaptive optical device capable of modifying the image emitted from the projector, and a processor capable of receiving the information related to aberrations introduced by the eye and adjusting the adaptive optical device to produce a corrected image. The corrective prescription verification method includes emitting the image of the scene and modifying the emitted image based on the information related to aberration introduced by the eye to produce a corrected image at the eye.

Yet another aspect of the present invention is a binocular wavefront measuring apparatus and method for determining aberrations in a pair of eyes at substantially the same time. The binocular wavefront measuring apparatus includes a first ophthalmic wavefront measuring device for measuring the aberrations introduced by a first eye of the pair of eyes and a second ophthalmic wavefront measuring device for measuring the aberrations introduced by a second eye of the pair of eyes. The binocular wavefront measuring method includes measuring the aberrations introduced by a first eye of the pair of eyes, measuring the aberrations introduced by a second eye of the pair of eyes, and determining a first corrective prescription for the first eye and a second corrective prescription for the second eye, wherein the aberrations of the first and second eyes are measured substantially simultaneously.

BRIEF DESCRIPTION OF THE DRAWINGS

FIG. 4 is a block diagram of an alternative wavefront measuring device with input beam modification in accordance with the present invention;

DETAILED DESCRIPTION OF THE INVENTION

Figure 3:
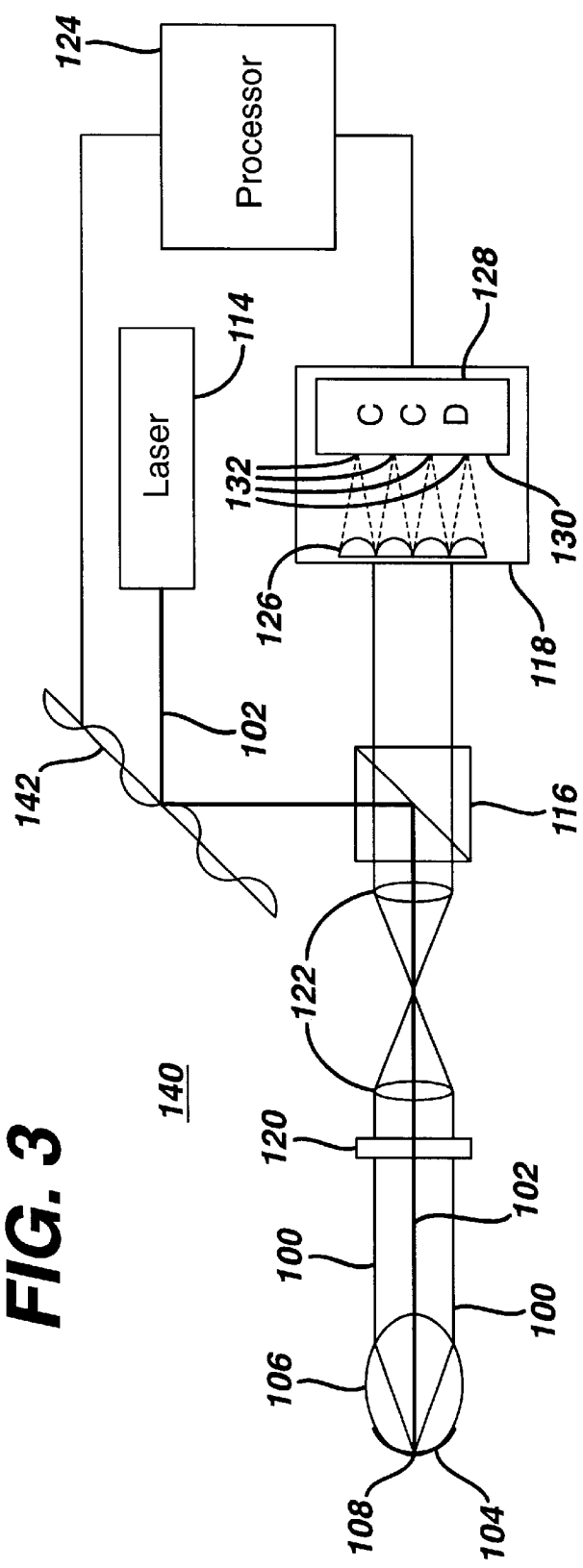
FIG. 3 is a block diagram of a wavefront measuring device with input beam modification in accordance with the present invention.

Illustrated in FIG. 3 is an ophthalmic wavefront measuring device 140 with input beam modification in accordance with the present invention. In a general overview, a radiation source 114 generates an input beam 102 which is modified by an adaptive optical device 142. A beam splitter 116 then redirects the input beam 102 toward an eye 106. The input beam 102 enters the eye 106 through the cornea where it is focused to a spot 108 on the retina 104 and reflected to produce a wavefront 100 that travels back out of the eye 106. The wavefront 100 is affected by defects within the eye 106 which cause aberrations. The affected wavefront 100 passes through the beam splitter 116 toward a sensor 118 which samples the wavefront 100 and captures information related to one or more images of the retinal spot 108 formed at the sensor 118. A processor 124 controls the adaptive optical device 142 to modify the input beam 102 to produce a desired image at the sensor 118.

Figure 1:
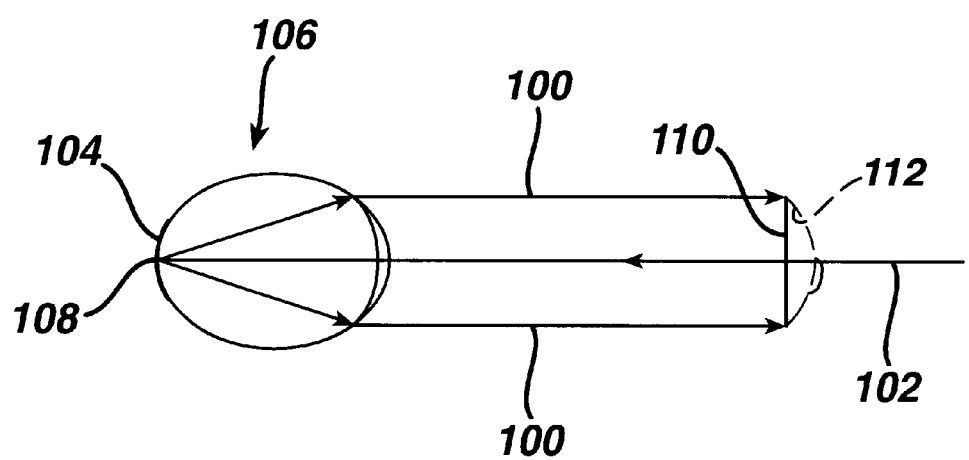
FIG. 1 is a schematic view of a wavefront generated by reflecting an input beam off of the retina of an eye.
Figure 2:
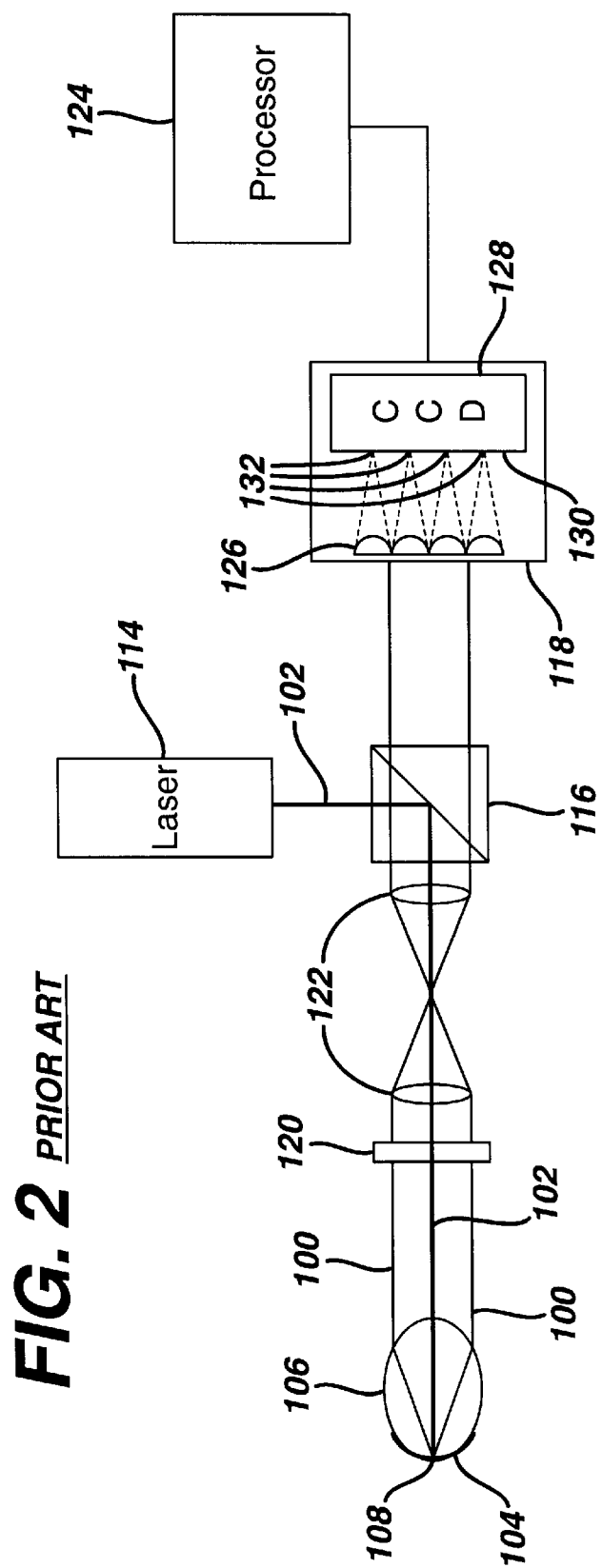
FIG. 2 is a block diagram of a prior art apparatus for measuring aberrations introduced by an eye.

The wavefront measuring device 140 is similar to the prior art wavefront measuring device depicted in FIG. 2 with the addition of the adaptive optical device 142 in the path of the input beam 102. The processor 124 modifies the input beam 102 using the adaptive optical device 142 based on feedback from the sensor 118 to produce the desired image at the sensor 118. In a preferred embodiment, the desired image has an easy to calculate centroid, thereby facilitating the determinations of aberrations in the wavefront 100. The wavefront measuring device 140 is now described in more detail below.

The radiation source 114 generates the input beam 102 by generating a collimated beam of photons, and is preferably a laser. Other suitable radiation sources for use with wavefront measuring devices are well known in the art.

The adaptive optical device 142 is capable of modifying the input beam 102 in response to a modification signal. As will be described below, in the illustrated embodiment, the processor 124 produces the modification signal based on information at the sensor 118. As one possible alternative, the adaptive optical device 142 may include a processor that configures the adaptive optical device 142 based on information from the sensor 118.

In the illustrated embodiment, the adaptive optical device 142 is a deformable mirror. The surface of the deformable mirror deforms in response to the modification signal to modify the input beam 102 as it is deflected off the deformed surface. Deformable mirrors for use in wavefront measuring devices are well known in the art. In alternative embodiments, the adaptive optical device 142 may be a liquid crystal device, a micro machine mirror, or other suitable device capable of modifying a beam of light.

The beam splitter 116 is a known device capable of selectively passing and directing beams of light. In the illustrated embodiment, the beam splitter 116 is configured to reflect the input beam 102 toward the eye 106, and to pass the wavefront 100 projecting from the eye 106 unaltered. Preferably, the beam splitter 116 is a polarizing beam splitter which selectively passes or reflects light based on the polarization of the light.

Figure 2A:
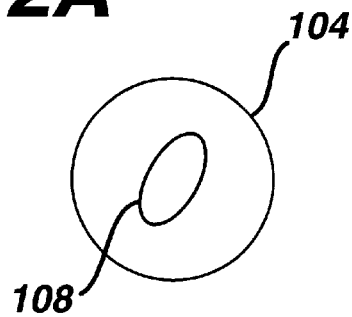
FIG. 2A is an illustrative representation of a spot formed on the retina of the eye in FIG. 2.
Figure 2B:
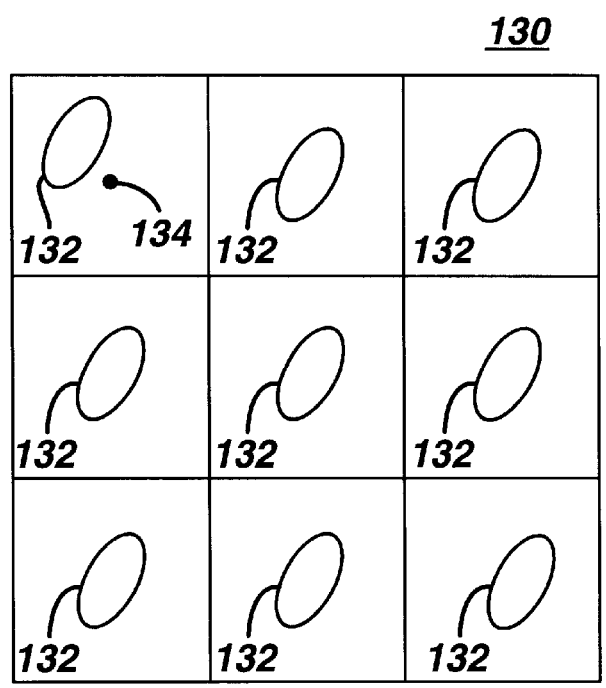
FIG. 2B is an illustrative representation of an array of spots produced by a sensor in the prior art apparatus of FIG. 2.

The eye 106 receives the input beam 102, and a wavefront 100 emanates from the eye 106 in response to the input beam 102. Here, the input beam 102 is focused to a spot 108 on the retina 104 of the eye 106. Ideally, as will be described below, the retinal spot 108 will be substantially circular to aid in computing the centroid of one or more images of the retinal spot 108 formed at the sensor 118. Due to imperfections within the eye 106 acting on the input beam 102 entering the eye 106, however, the retinal spot 108 may be irregular (e.g., non-circular), as depicted in FIG. 2A.

A quarter-wave plate 120 and lenses 122, are positioned between the eye 118 and the sensor 118. The quarter-wave plate 120 converts linearly polarized light to circularly polarized light and vice versa to condition the light in and out of the eye 106 in a known manner such that the beam splitter 116 can appropriately direct the input beam 102 and the wavefront 100. The lenses 122 direct the wavefront 100 between the eye 106 and the sensor 118 in a known manner to image the plane of the pupil of the eye 106 onto the sensor 118 with a desired magnification. The quarter-wave plate 120 and the lenses 122 are well known in the art.

Figure 3A:
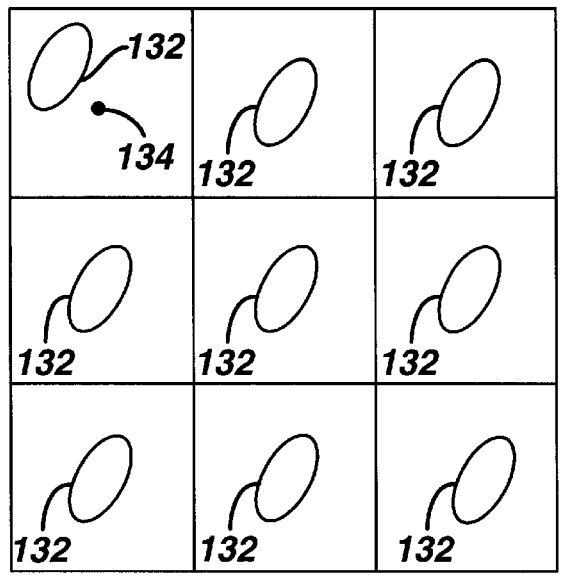
FIG. 3A is an illustrative representation of an array of spots produced by the sensor of FIG. 3 without input beam modification.

The sensor 118 is a conventional sensor for sensing an image of the retinal spot 108 within the wavefront 100 emanating from the eye 106. In the illustrated embodiment, the sensor 118 includes a Hartman-Shack lenslet array 126 and an imaging device 128, e.g., a CCD camera. The lenslet array 126 focuses portions (i.e., samples) of the wavefront 100 onto an imaging plane 130 of the imaging device 128. The imaging device 128 is capable of precisely detecting the location of energy incident to the imaging plane 130 and generating information related to the location of energy for processing by the processor 124. As depicted in FIGS. 3 and 3A, the lenslet array 126 forms a plurality of images 132 of the retinal spot 108 on the imaging plane 130 of the imaging device 128 with each of the plurality of images representing the aberration in a corresponding sample of the wavefront 100. In a preferred embodiment, the sensor 118 senses an image of the retinal spot 108 in at least one sample of the wavefront 100.

Figure 3B:
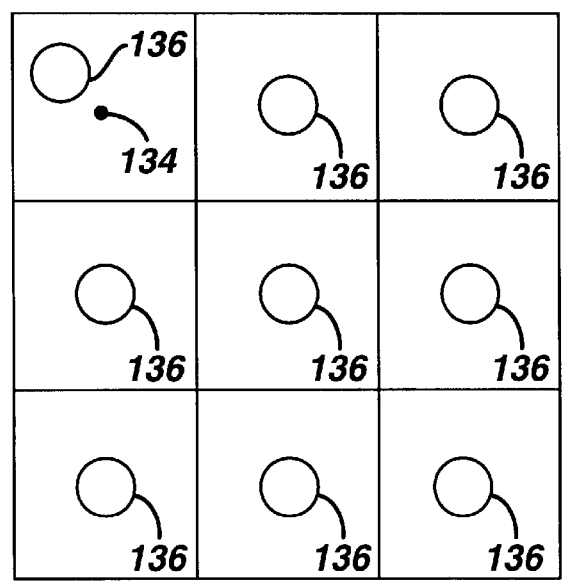
FIG. 3B is an illustrative representation of an array of spots produced by the sensor of FIG. 3 with input beam modification in accordance with the present invention.

The processor 124 adjusts the adaptive optical device 142 based on information received from the sensor 118. The processor 124 receives information related to an image of the retinal spot 108 on the imaging plane 130 of the sensor 118 in at least one sample of the wavefront 100 from the sensor 118 and analyzes the information to compute a modification signal for adjusting the adaptive optical device 142 to modify the input beam 102 and thereby produce a desired image on the imaging plane 130 of the sensor 118. For example, if the desired image were a circle, the processor 124 would modify the input beam 102 by adjusting the adaptive optical device 142 until circular spots 136 appeared on the imaging plane 130 as depicted in FIG. 3B.

The processor 124 is a conventional processor configured for analyzing the information from sensor 118 to produce a modification signal for adapting the adaptive optical device 142. The processor 124 may also determine a corrective prescription for correcting aberrations sensed by the sensor 118 using conventional aberration correction software.

In use, the wavefront measuring device 140 is able to precisely and efficiently determine aberrations for samples of the wavefront 100. As discussed above, the aberrations of the wavefront 100 are typically determined by determining the aberration of each sample of the wavefront 100 and combining the aberrations for all of the samples. The aberrations of the individual samples are determined by determining the displacement between the centroid of each of the plurality of images 132 and a corresponding reference location, such as the location represented by reference spot 134. Determining the centroid of an irregular spot such as one of the plurality of images 132, however, requires a significant amount of processing time and power and/or may be impossible to determine as precisely as if the spot were circular.

In order to simplify processing and provide more precise measurement of the centroid, the processor 124 generates the modification signal based on the information from the sensor 118 to adjust the adaptive optical device 142 and thereby modify the input beam that, in turn, modifies the retinal spot 108 that, in turn, modifies the image at the sensor 118. The processor 124 updates the modification signal based on feedback from the sensor 118 until a desired image is sensed at the sensor 118. In a preferred embodiment, the image produced at the sensor 118 is an image for which the centroid is easy to determine, such as the substantially circular images 136 in FIG. 3B. Since it is easier to determine precisely the centroid of a substantially circular image than an irregular image, producing desired images such as the circular images 136 at the imaging plane 132 increases precision while simplifying the determination of the centroid in a wavefront measuring device 140, thereby improving and facilitating the determination of aberrations by the wavefront measuring device 140.

FIG. 4 depicts an alternative embodiment of a wavefront measuring device with input beam correction. The wavefront measuring device depicted in FIG. 4 is identical to the wavefront measuring device depicted in FIG. 3 with the addition of another beam splitter 144 and sensor 146. The additional beam splitter 144 and sensor 146 are used to provide information regarding the image of the retinal spot 108 at the sensor 146 to the processor 124 that, in turn, controls the adaptive optical device 142 to modify the input beam 102 to produce a desired image at the sensor 146. The image of the retinal spot 108 formed on the sensor 146 will have the same shape as the plurality of images of the retinal spot 108 formed at the sensor 118. Therefore, by modifying the input beam 102 to produce a desire shape at the sensor 146, the same desired shape will be produced at the sensor 118.

As discussed above, if the desired shape is a shape for which the centroid can be easily determined, such as a circular shape, the centroid of the desired shape can be determined precisely and easily. Accordingly, since the determination of the centroid is required to determine aberrations in the wavefront 100, precision and efficiency are increased in the determination of the aberrations by a wavefront measuring device.

The beam splitter 144 is a conventional beam splitter capable of selectively passing and directing beams. In the illustrated embodiment, the beam splitter 144 is configured in a known manner to allow a portion of the wavefront 100A to pass through the beam splitter 144 to the sensor 118 and reflect a portion of the wavefront 100B toward the sensor 146. Preferably, the beam splitter 144 is a polarizing beam splitter which selectively passes or reflects light based on the polarization of the light.

The sensor 146 senses the image of the retinal spot 108 within the wavefront 100 emanating from the eye 106. In the illustrated embodiment, the sensor 146 includes a single lens 148 and an imaging device 150, e.g., a CCD camera. The imaging device 150 is capable of precisely detecting the location of energy incident to an imaging plane 152 and generating information regarding the location of the energy. The information regarding the location of the energy is passed to the processor 124 for adjusting the adaptive optical device 142 as discussed above in reference to FIG. 3.

Figure 4A:
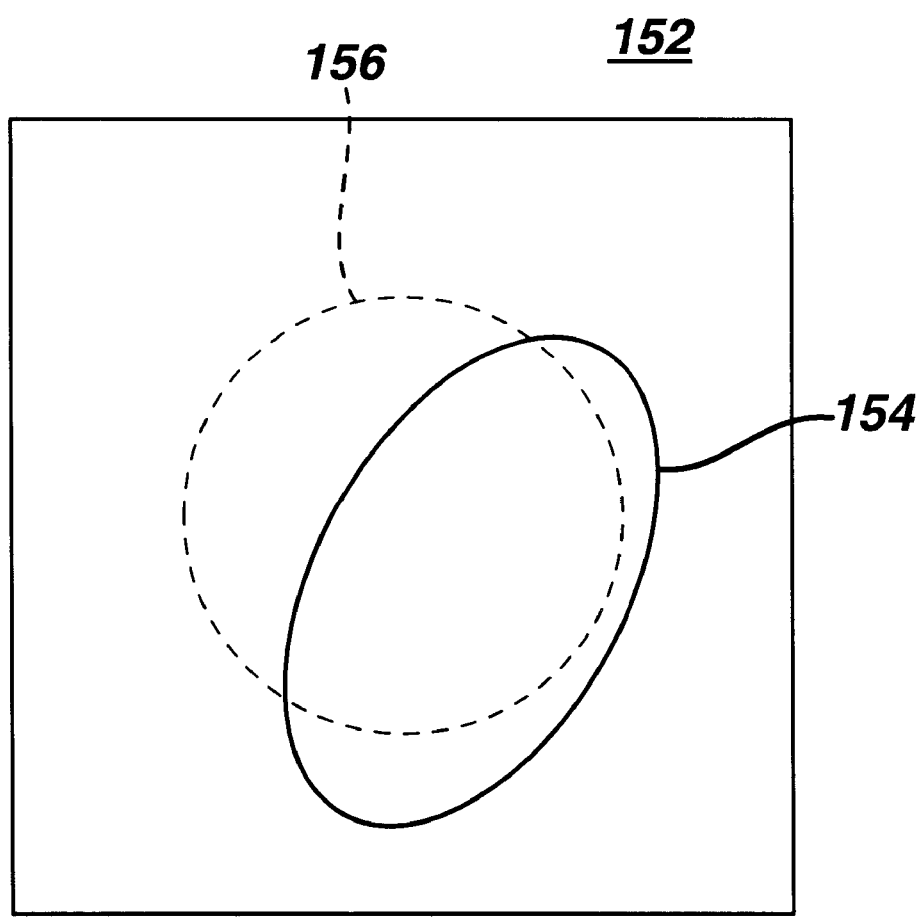
FIG. 4A is an illustrative representation of an image of a spot on the retina formed on an imaging plane in the alternative wavefront measuring device of FIG. 4.

As depicted in FIGS. 4 and 4A, the single lens 148 forms a single image 154 of the retinal spot 108 on the imaging plane 152 of the imaging device 150 by focusing a portion of the wavefront 100B onto the imaging plane 152 of the imaging device 150. In contrast to the embodiment depicted in FIG. 3 where the same lenslet array 126 and imaging device 128 are used for modifying the input beam 102 and measuring aberrations, the single lens 148 and imaging device 150 are dedicated to providing feedback related to an image of the retinal spot 108 formed on the imaging plane 152. This allows the focal length of the lens 148 and the sensitivity of the imaging device 150 to be selected for providing feedback related to the shape of the image of the retinal spot 108, thereby permitting the development of a more specialized input beam correction device than the one depicted in FIG. 3.

In use, the wavefront measuring device depicted in FIGS. 4 and 4A, uses the adaptive optical device 142 to modify the input beam 102 to produce an image of the retinal spot 108 on the imaging plane 152 which has a desired shape, such as the substantially circular shape 156 on the imaging plane 152. Modifying the input beam 102 to produce a desired shape on the imaging plane 152 results in a plurality of desired shapes being formed on the imaging plane 130 of sensor 118 for which the centroid is easier to determine. For example, modifying the input beam 102 to produce a circular shape 156 on the imaging plane 152 results in a plurality of circular spots being formed on the imaging plane 130. Since, as discussed above, it is easier to determine precisely the centroid of a substantially circular image than an irregular image, the determination of the centroid is simplified, thereby simplifying the determination of the aberrations by the wavefront measuring device of FIG. 4.

Figure 5:
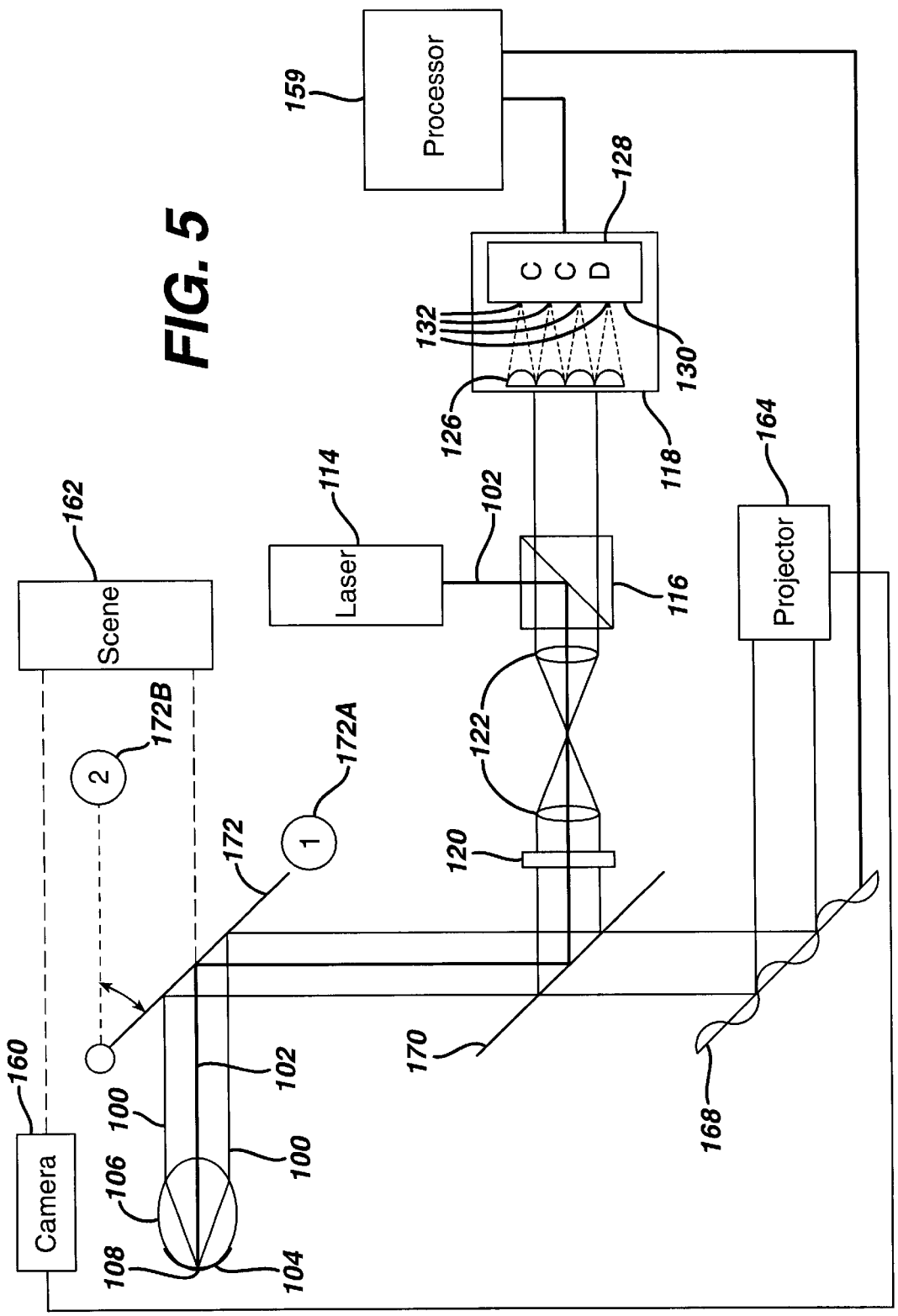
FIG. 5 is a block diagram of a wavefront measuring device with corrective prescription verification capabilities in accordance with the present invention.

FIG. 5 depicts a preferred corrective prescription verification device for use with a wavefront measuring device. The corrective prescription verification device allows a patient to visually verify a corrective prescription determined by the wavefront measuring device prior to the formation of a corrective lens.

The wavefront measuring device depicted in FIG. 5 is similar to the wavefront measuring device depicted in FIG. 2, accordingly, only the additional components will be described in detail. The additional components include a camera 160 for capturing an image of a scene 162, a projector 164 for emitting an image of the scene 162, an adaptive optical device 168 for modifying the emitted image, a processor 159 for controlling the adaptive optical device 168, a dichroic mirror 170 for reflecting the input beam 102 and placing the image of the scene 162 on the same path as the input beam 102, and a movable mirror 172 for reflecting the image of the scene 162 to the eye 106 when in a first position 172A and allowing the eye 106 to view the scene 162 directly when in a second position 172B.

In a general overview, a radiation source 114 generates an input beam 102 which is redirected by a beam splitter 116, then reflected by a dichroic mirror 170, and then reflected again by a movable mirror 172 (when in a first position 172A) toward the eye 106. The input beam 102 enters the eye 106 where it is reflected by the retina 104 to produce a wavefront 100 that travels back out of the eye 106. The wavefront 100 is affected by defects within the eye 106 which cause aberrations. The wavefront 100 passes back through the movable mirror 172 and the dichroic mirror 170 toward a sensor 118. The wavefront 100 passes through the beam splitter 116 toward the sensor 118 that captures information related to the wavefront and a processor 159 processes the information. The input beam 102 may be modified as discussed above with reference to FIGS. 3 and 4.

Meanwhile, a camera 160 captures an image of a scene 162 that is then projected by the projector 164. The projected image is modified by the adaptive optical device 168 that is adjusted by the processor 159 based on information from the sensor 118. The modified image is then combined with the input beam 102 by the dichroic mirror 170 and passed to the eye 106. The processor 159 adjusts the adaptive optical device 168 based on information from the sensor 118 to produce a corrected image at the eye 106. A corrected image is an image that is intentionally aberrated to appear to a patient as if it were corrected without the use of corrective lenses by the patient.

In reference to FIG. 5, more specifically, the scene 162 is a scene which can be viewed by a patient, e.g., an eye chart, picture, statue, or essentially any two or three dimensional object. The camera 160 is a conventional camera capable of capturing images and the projector 164 is a conventional projector capable of projecting an image of a scene. Preferably, the projector 164 includes a conventional lens for collimating the emitted image. Alternatively, known mirrors may be used to collimate the emitted image. Suitable cameras and projectors for use with the present invention are well known to those in the art.

The adaptive optical device 168 is a device capable of modifying the image projected by the projector 164 based on a correction signal. As will be described below, the processor 159 produces the correction signal based on information at the sensor 118 that is fed back to the adaptive optical device 168 to adjust the adaptive optical device 168, thereby modifying the projected image and producing a corrected image at the eye 106. The adaptive optical device 168 may be a deformable mirror such as the type described for the adaptive optical device 142 above.

The processor 159 controls the adaptive optical device 168. It receives information from the sensor 118 and analyzes the information to compute a correction signal for adjusting the adaptive optical device 168 for appropriately modifying the projected image to produce a corrected image for the eye 106. The processor 159 can be a conventional processor configured to run software for analyzing the information from the sensor 118 to produce a correction signal for adjusting the adaptive optical device 168.

The dichroic mirror 170 is a conventional optical device which passes light of one frequency and reflects light of other frequencies. In the preferred embodiment, the dichroic mirror 170 reflects the frequency of light from the radiation source 114 and passes the frequencies of light projected by the projector 164, thereby combining the input beam 102 and the projected image onto the same light path toward the eye 106.

The movable mirror 171 is a conventional mirror that reflects the input beam and the projected image toward the eye 106 when in a first position 172A and allows the eye 106 to view the scene 162 directly when in a second position 172B. When the movable mirror 171 is in the first position 172A, the wavefront measuring device of FIG. 5 can determine the aberrations introduced by the eye 106 and modify the image emitted by the projector 164 for viewing by the eye 106. When the movable mirror 171 is in the second position 172B, the eye 106 can view the scene directly, thereby providing the eye with a reference for comparing to the corrected image.

In use, the wavefront measuring device depicted in FIG. 5 provides feedback to the patient's eye 106 regarding a corrective prescription determined by the wavefront measuring device, thereby allowing a patient to verify the corrective prescription. Initially, the movable mirror 172 is positioned in the second position 172B to allow the patient to view the scene 162 directly. The movable mirror 172 is then positioned in the first position 172A to determine a corrective prescription, modify the image of the scene, and present a corrected image to the eye 106. The patient can then verify the accuracy of the corrective prescription determined by the wavefront measuring device of FIG. 5.

Figure 6:
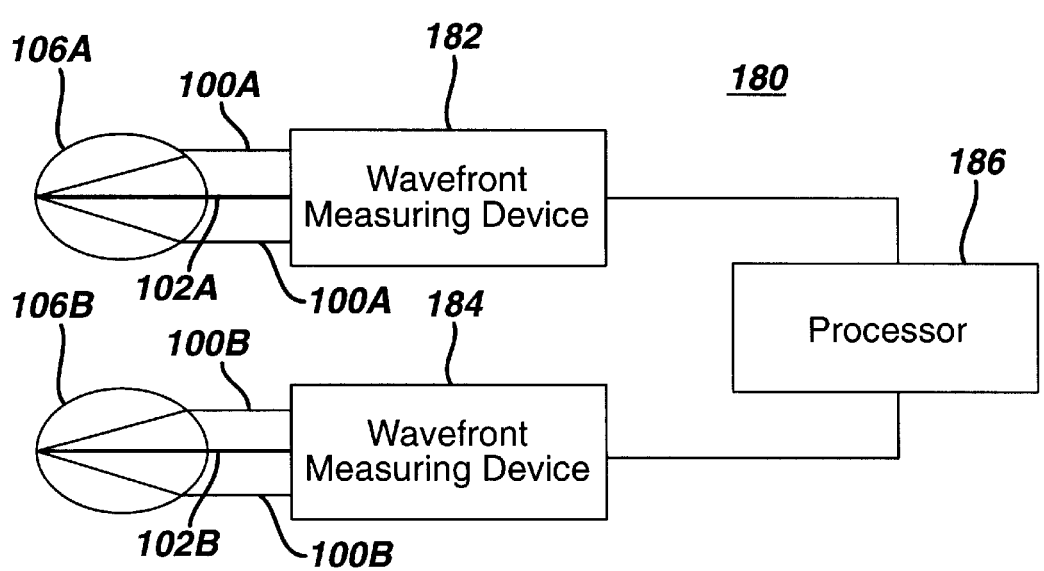
FIG. 6 is a block diagram of a binocular wavefront measuring apparatus in accordance with the present invention.

FIG. 6 depicts a binocular wavefront measuring apparatus 180 including a first conventional wavefront measuring device 182, a second conventional wavefront measuring device 184, and a processor 186. It is known that aberrations are affected by binocular vision (i.e., viewing something with both eyes). Therefore, to determine a corrective prescription for a pair of eyes, which corrects aberrations when viewing with both eyes, both eyes need to be measured at the same time. The binocular wavefront measuring apparatus illustrated in FIG. 6 enables the aberrations of both eyes to be determined substantially simultaneously, thereby allowing the aberrations, which are dependent on binocular vision, to be accurately determined for a pair of eyes 106A and 106B.

The first wavefront measuring device 182 measures aberrations introduced by the eye 106A. The first wavefront measuring device 182 generates an input beam 102A which is directed into the eye 106A and measures the aberrations in a wavefront 100A emanating from the eye 106A in response to the input beam 102A. The first wavefront measuring device 182 senses the aberrations introduced by the first eye 106A and generates information related to the aberrations for processing by the processor 186.

The second wavefront measuring device 184 measures aberrations introduced by the eye 106B in a similar manner, using an input beam 102B which is directed into the eye 106B and measuring the aberrations in a wavefront 100B emanating from the eye 106B in response to the input beam 102B. The second wavefront measuring device 184 senses the aberrations introduced by the second eye 106B and generates information related to the aberrations for processing by the processor 186.

The processor 186 is a conventional processor for processing the information from the two conventional wavefront measuring devices 182 and 184 related to the eyes 106A and 106B, respectively, to determine a corrective prescription for the pair of eyes 106A and 106B. The processor 186 captures information generated by the wavefront measuring devices 182 and 184 regarding the aberrations introduced by each eye 106A and 106B, respectively, substantially simultaneously, thereby capturing the aberrations, including those that may be affected by binocular vision.

The processor 186 may include a single processor for processing information for each eye 106A and 106B, or the processor 186 may include a plurality of processors such as one processor for processing information related to one of the eyes 106A and another processor processing information related to the other eye 106B. The software used by the processor 186 can be selected from conventional software for determining wavefront aberrations and modified for use with two wavefront measuring devices 182 and 184. The modification of the conventional software for use with the binocular wavefront measuring apparatus depicted in FIG. 6 is within the level of ordinary skill in the art.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A corrective prescription verification apparatus for use with an ophthalmic wavefront measuring device capable of generating information related to aberrations introduced by an eye, said apparatus comprising:

a projector capable of emitting an image wherein said image is produced by a camera capable of capturing said image from a scene;

an adaptive optical device capable of modifying said image emitted from said projector;

a processor capable of receiving the information related to aberrations introduced by the eye and adjusting said adaptive optical device to produce a corrected image; and a movable mirror having a first position and a second position, said moveable mirror directing said image to the eye when in said first position and allowing the eye to view the scene directly when in said second position.

2. A corrective prescription verification method for displaying a scene to a patient for use with an ophthalmic wavefront measuring device capable of generating information related to aberrations introduced by an eye of the patient, said method comprising the steps of:

capturing an image of the scene;

emitting said image of the scene;

modifying said emitted image based on the information related to the aberrations introduced by the eye to produce a corrected image at the eye;

directing said image to the eye when a movable mirror is in a first position; and allowing the eye to view the scene directly when said movable mirror is in a second position.

* * * * *